(12) United States Patent
Lebret et al.

(10) Patent No.: US 7,749,767 B2
(45) Date of Patent: Jul. 6, 2010

(54) USE OF SILOXANE-BASED POLYMERS OR COMPOSITES IN CHEMICAL SENSOR FOR DETECTING NITRATE COMPOUNDS

(75) Inventors: Bruno Lebret, Chambray-les-Tours (FR); Lionel Hairault, La Croix en Touraine (FR); Eric Pasquinet, Saint Avertin (FR)

(73) Assignee: Commissariat a l'Energie Atomique, Paris (FR)

( * ) Notice: Subject to any disclaimer, the term of this patent is extended or adjusted under 35 U.S.C. 154(b) by 535 days.

(21) Appl. No.: 10/581,216

(22) PCT Filed: Dec. 3, 2004

(86) PCT No.: PCT/FR2004/050646

§ 371 (c)(1), (2), (4) Date: Mar. 23, 2007

(87) PCT Pub. No.: WO2005/057198

PCT Pub. Date: Jun. 23, 2005

(65) Prior Publication Data

US 2007/0178600 A1    Aug. 2, 2007

(30) Foreign Application Priority Data

Dec. 5, 2003    (FR) .................................. 03 50984

(51) Int. Cl.
*G01N 33/00* (2006.01)
(52) U.S. Cl. .................... 436/107; 436/106; 422/50; 524/588
(58) Field of Classification Search .................. 524/588; 422/82.01, 82.02, 98, 68.1, 102
See application file for complete search history.

(56) References Cited

U.S. PATENT DOCUMENTS

| 6,387,329 B1 * | 5/2002 | Lewis et al. .................... 422/98 |
| 6,433,694 B1 | 8/2002 | Dolan et al. |
| 2003/0165407 A1 * | 9/2003 | Aker et al. .................... 422/88 |
| 2003/0168355 A1 | 9/2003 | Houser et al. |

FOREIGN PATENT DOCUMENTS

| DE | 197 08 529 | 7/1998 |
| FR | 2 815 351 | 4/2002 |
| WO | 98/22795 | 5/1998 |
| WO | 01/77664 | 10/2001 |
| WO | 02/08234 | 1/2002 |
| WO | 02/23134 | 3/2002 |

OTHER PUBLICATIONS

Ali, M.B. et al., "Sensitive Cyclodextrin-Polysiloxane Gel Membrane On EIS Structure And ISFET For Heavy Metal Ion Detection", Sensors and Actuators B, vol. 62, No. 3, pp. 233-237, 2000.

Content, S. et al., "Detection of Nitrobenzene, DNT, and TNT Vapors by Quenching of Porous Silicon Photoluminescence", Chem. Eur. J., vol. 6, No. 12, pp. 2205-2213, 2000.

McGill, R.A. et al., "The Design Of Functionalized Silicone Polymers For Chemical Sensor Detection Of Nitroaromatic Compounds", Sensors and Actuators B, vol. 65, No. 1-3, pp. 5-9, 2000.

Nelli, P. et al., "Cavitands as Selective Materials for QMB Sensors for Nitrobenzene and Other Aromatic Vapours", Sensors and Actuators B, vol. 13, No. 1/3, pp. 302-304, 1993.

Sanchez-Pedreno, J.A.O. et al., "The Investigation Of Coating Materials For The Detection Of Nitrobenzene With Coated Quartz Piezoelectric Crystals", Analytica Chimica Acta, vol. 182, pp. 285-291, 1986.

Yang, X. et al., "Growth Of Ultrathin Covalently Attached Polymer Films: Uniform Thin Films For Chemical Microsensors", Langmuir, vol. 14, No. 7, pp. 1505-1507, 1998.

Yang, J. et al., "Fluorescent Porous Polymer Films as TNT Chemosensors: Electronic and Structural Effects", J. Am. Chem. Soc., vol. 120, pp. 11864-11873, 1998.

\* cited by examiner

*Primary Examiner*—Yelena G Gakh
*Assistant Examiner*—David Weisz
(74) *Attorney, Agent, or Firm*—Nixon & Peabody LLP

(57) ABSTRACT

The invention relates to the use of at least one polymer comprising a repeating unit of formula (I):

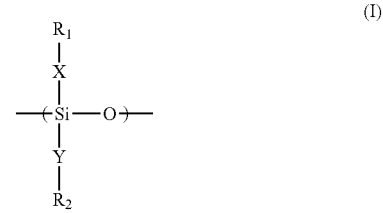

in which:
X and Y=single bond or linear $C_1$-$C_{50}$ hydrocarbon group;
$R_1$ and $R_2$=H, CN, $C(Z)_3$, $CH(Z)_2$, $CH_2Z$ with Z=halogen; $NH_2$, $NHR_3$, $NR_3R_4$ with $R_3$, $R_4$=halogen, $CH_3$ or linear or branched, saturated or unsaturated $C_2$-$C_{20}$ hydrocarbon chain, optionally comprising one or more heteroatoms and/or chemical functions comprising at least one heteroatom; at least one from among $R_1$ and $R_2$ being ≠H;

or of a composite comprising this polymer and one or more conductive charges, as sensitive material in a sensor for detecting nitro compounds.

Applications: Detection of explosives, control/monitoring of atmospheric pollution and of ambient air quality, monitoring of industrial sites.

19 Claims, 3 Drawing Sheets

USE OF SILOXANE-BASED POLYMERS OR COMPOSITES IN CHEMICAL SENSOR FOR DETECTING NITRATE COMPOUNDS

CROSS-REFERENCE TO RELATED APPLICATION

This application claims priority based on International Patent Application No. PCT/FR2004/050646, entitled "Use of Siloxane-Based Polymers Or Composites In Chemical Sensors For Detecting Nitrate Compounds" by Bruno Lebret, Lionel Hairault and Eric Pasquinet, which claims priority of French Application No. 03 50984, filed on Dec. 5, 2003, and which was not published in English.

TECHNICAL FIELD

The present invention relates to the use of siloxane-based polymers or of composites comprising such a polymer and one or more electrically conductive fillers as sensitive materials in sensors for detecting nitro compounds, and in particular nitroaromatic compounds such as nitrobenzene (NB), dinitrobenzene (DNB), trinitrobenzene (TNB), nitrotoluene (NT), dinitrotoluene (DNT), 2,4,6-trinitrotoluene (TNT) and the like.

Such sensors are useful for detecting explosives, whether for the purpose of ensuring the safety of public places such as airports, for checking the legality of merchandise in circulation in a territory, for combating terrorism, for performing disarmament operations, for locating antipersonnel mines or for decontaminating industrial or military sites.

They are also useful for environmental protection, in particular for controlling and monitoring atmospheric pollution and the quality of more of less confined atmospheres, and also for the monitoring, for security purposes, of industrial sites that manufacture, store and/or handle nitro compounds.

PRIOR ART

The detection of explosives is a problem of vital importance, especially in terms of civil safety.

At the present time, several methods are used for detecting vapors of nitro compounds used in the preparation of explosives, for instance the use of sniffer dogs trained for this purpose, laboratory analysis, for example by chromatography coupled with a mass spectrometer or with an electronic trap detector, of samples collected on site, or alternatively infrared detection.

These methods generally show great sensitivity, which is fundamental in terms of detecting explosives, given the very low concentration of vapors of nitro compounds that prevails in the vicinity of an explosive. However, they are not entirely satisfactory.

Thus, the use of sniffer dogs has the drawback of requiring long training of the dogs and of their handlers, and of being unsuitable for prolonged operations due to the fact that the attention span of dogs is limited.

As regards the other methods, the physical bulk of the apparatus they use, their energy consumption and their operating costs run counter to the development of detection systems that are easily transportable and autonomous and, consequently, able to be used on sites of any type.

In recent years, the development of sensors capable of the real-time detection of gaseous chemical species is in full expansion. The functioning of these sensors is based on the use of a film of a sensitive material, i.e. a material for which at least one physical property is modified on contact with the gaseous molecules sought, which amounts to a system capable of the real-time measurement of any variation of this physical property and thus of demonstrating the presence of the gaseous molecules sought.

The advantages of chemical sensors over the other above-mentioned methods are manifold: immediacy of the results, possibility of miniaturization and therefore great portability, handleability and autonomy, low manufacturing and operating costs, etc.

However, it is obvious that their efficiency is extremely variable depending on the nature of the sensitive material used.

For the detection of gaseous nitro compounds, and more particularly of nitroaromatic compounds, many sensitive materials have already been proposed, among which mention may be made of porous silicon, plant charcoal, polyethylene glycol, amines, cyclodextrins, cavitands and fluorescent polymers (references [1] to [5]).

Moreover, the potential use of functionalized polysiloxanes as sensitive materials for sensors intended for detecting nitroaromatic compounds has been studied by McGill et al. (reference [6]).

These authors focused on determining the solubility parameters of a number of nitroaromatic compounds (NB, NT, TNB, DNT and TNT) and on defining, from these parameters, their sorption properties in the vapor state (i.e. their ability to be absorbed and retained) in a series of polymers including various polysiloxanes.

McGill et al. deduce from the results they obtain that nitroaromatic compounds are capable of interacting with polymers proportionately more strongly when these polymers have solubility parameters that are complementary to those of said nitroaromatic compounds. They conclude therefrom that the most promising polysiloxanes for detecting nitroaromatic compounds are those whose monomers comprise an aromatic ring bearing one or more groups capable of establishing hydrogen bonds with these compounds, for example a hexafluoroisopropanol (HFIP) group. It is a fact that the DNT detection tests they perform using a sensor with surface waves equipped with a thin film of a polysiloxane derived from monomers containing an aromatic ring bearing an HFIP side group appear to give satisfactory results.

However, in the context of their studies on the development of sensors more especially intended for detecting explosives, the inventors have found that, entirely surprisingly, sensors using, as sensitive materials, siloxane-based polymers that comprise neither an aromatic ring nor a side group of HFIP type detect nitro compounds, and in particular nitroaromatic compounds, with a markedly higher sensitivity than sensors using the polysiloxanes recommended by McGill et al.

This finding is the basis of the invention.

DESCRIPTION OF THE INVENTION

One subject of the invention is the use of at least one polymer comprising at least one siloxane repeating unit corresponding to the general formula (I) below:

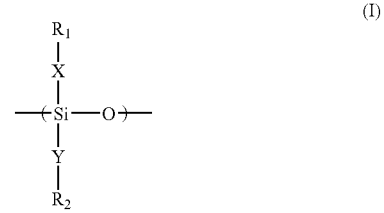

in which:

X and Y, which may be identical or different, represent a single bond or a saturated or unsaturated, linear hydrocarbon group containing from 1 to 50 carbon atoms;

$R_1$ and $R_2$, which may be identical or different, represent a hydrogen atom, a CN group, a group $C(Z)_3$, $CH(Z)_2$ or $CH_2Z$ with Z representing a halogen atom; an $NH_2$ group, a group $NHR_3$ or $NR_3R_4$ with $R_3$ and $R_4$ representing, independently of each other, a halogen atom, a methyl group or a linear or branched, saturated or unsaturated hydrocarbon chain containing from 2 to 20 carbon atoms and possibly one or more heteroatoms and/or one or more chemical functions comprising at least one heteroatom; on condition, however, that at least one from among $R_1$ and $R_2$ is not a hydrogen atom; or of a composite comprising this polymer and one or more electrically conductive fillers, as sensitive material in a sensor for detecting one or more nitro compounds.

In the general formula (I) above, when $R_3$ and/or $R_4$ represent a $C_2$ to $C_{20}$ hydrocarbon chain and when this chain comprises one or more heteroatoms and/or one or more chemical functions, then these atoms and these functions may either form a bridge within this chain or may be borne laterally thereby, or alternatively may be located at the end thereof.

The heteroatom(s) may be any atom other than a carbon or hydrogen atom, for instance an oxygen, sulfur, nitrogen, fluorine, chlorine, phosphorus, boron or silicon atom.

The chemical function(s) may be chosen especially from —COOH, —COOR$_5$, —CHO, —CO—, —OH, —OR$_5$, —SH, —SR$_5$, —SO$_2$R$_5$, —NH$_2$, —NHR$_5$, —NR$_5$R$_6$, —CONH$_2$, —CONHR$_5$, —CONR$_5$R$_6$, —C(Z)$_3$, —OC(Z)$_3$, —COZ, —CN, —COOCHO and —COOCOR$_5$ functions in which:

$R_5$ represents a linear or branched, saturated or unsaturated hydrocarbon group containing from 1 to 100 carbon atoms, or a covalent bond when said chemical function(s) form(s) a bridge in a $C_2$ to $C_{20}$ hydrocarbon chain;

$R_6$ represents a linear or branched, saturated or unsaturated hydrocarbon group containing from 1 to 100 carbon atoms, this group possibly being identical to or different from the hydrocarbon group represented by $R_5$; while Z represents a halogen atom, for example a fluorine, chlorine or bromine atom.

Moreover, in the general formula (I), when X and/or Y represents a single bond, then $R_1$ and/or $R_2$ are respectively linked directly to the silicon atom via a covalent bond such that the siloxane repeating unit corresponds to one of the particular formulae (Ia), (Ib) and (Ic) below:

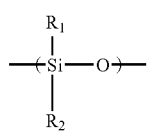

(Ia)

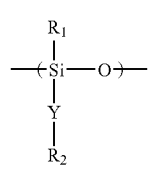

(Ib)

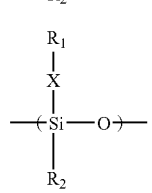

(Ic)

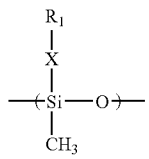

in which X, Y, $R_1$ and $R_2$ have the same meaning as above.

According to one preferred arrangement of the invention, the siloxane repeating unit corresponds to the particular formula (Id) below:

(Id)

in which X is a saturated or unsaturated linear hydrocarbon group containing from 1 to 50 carbon atoms, while $R_1$ has the same meaning as above.

Among the siloxane repeating units of particular formula (Id) that are especially preferred are those in which X represents an alkylene chain containing from 2 to 10 carbon atoms (i.e. a chain $(CH_2)_n$ in which n ranges from 2 to 10) and, among these units, trifluoropropylmethylsiloxane (X=$(CH_2)_2$, $R_1$=$CF_3$) and cyanopropylmethylsiloxane (X=$(CH_2)_3$, $R_1$=CN).

According to another preferred arrangement of the invention, the polymer is a homopolymer, i.e. it consists of only one siloxane repeating unit of general formula (I), in which case it is advantageously chosen from polytrifluoropropylmethylsiloxanes and polycyanopropylmethylsiloxanes, and more particularly from those with an average molecular weight ranging from 50 to 100 000.

As a variant, the polymer may also be a copolymer, in which case it may either consist of different siloxane repeating units all corresponding to the general formula (I) or comprise one or more siloxane repeating units of general formula (I) and one or more other, siloxane or non-siloxane, repeating units.

Specifically, it may be useful, for example, to include in the polymer repeating units derived from a monomer of the type such as ethylene, propylene, ethylene oxide, styrene, vinylcarbazole or vinyl acetate, which are capable of giving it better mechanical strength especially when it is desired to use it in the form of a thin film.

Since the polymers containing a siloxane repeating unit of the general formula (I) are not intrinsically electrically conductive, it is possible, in accordance with the invention, to mix them with one or more conductive fillers in an amount that is sufficient for the resulting composites to have an electrical conductivity suited to their use as sensitive materials of resistive sensors. These conductive fillers may be, for example, carbon black particles or metal (Cu, Pd, Au, Pt, etc.) or metal oxide ($V_2O_3$, TiO, etc.) powders.

According to yet another preferred arrangement of the invention, the polymer or the composite is in the form of a thin film that covers one or both faces of a substrate suitably chosen as a function of the physical property of the sensitive material whose variations are intended to be measured by this sensor.

As a variant, the polymer or the composite may also be in a bulk form, for instance a cylinder having a certain porosity so as to make all of the molecules forming said polymer or said composite available to the nitro compounds.

When it is in the form of a thin film, this film is preferably from 10 angstroms to 100 microns thick.

Such a film may be obtained via any of the techniques proposed to date for preparing a thin film on the surface of a substrate, for example:

- by spraying, by spin coating or by drop coating of a solution containing the polymer or the composite onto the substrate,
- by dip coating of the substrate in a solution containing the polymer or the composite,
- via the Langmuir-Blodgett technique,
- by electroplating, or
- by polymerization in situ, i.e. directly onto the surface of the substrate, of a precursor monomer of the polymer.

The substrate and the measuring system of the sensor are chosen as a function of the physical property of the polymer or of the composite whose variations induced by the presence of nitro compounds are intended to be measured by the sensor.

In the present case, the variations of two physical properties proved to be particularly advantageous to measure: the variations in mass in the case of a polymer and the variations in electrical conductivity in the case of a composite.

Thus, the sensor is preferably a gravimetric sensor for measuring variations in mass, or a resistive sensor for measuring variations in electrical conductivity.

Examples of gravimetric sensors that may be mentioned include sensors of the quartz microbalance type, surface acoustic wave (SAW) sensors, such as Love wave sensors and Lamb wave sensors, and also microlevers.

Among the gravimetric sensors that are more particularly preferred are sensors of the quartz microbalance type. This type of sensor, the operating principle of which is described in reference [2], comprises, schematically, a piezoelectric substrate (or resonator), generally a quartz crystal covered on its two faces with a layer of metal, for example of gold or platinum, and which is connected to two electrodes. Since the sensitive material covers one or both faces of the substrate, any variation in the mass of this material is reflected by a variation in the vibration frequency of the substrate.

Needless to say, it is also possible to use a polymer or a composite as defined previously, as sensitive material in sensors designed to measure variations in a physical property other than the mass and the electrical conductivity, for instance variations in an optical property such as fluorescence, luminescence, absorbance in the UV-visible range or wavelength in the infrared range.

In this case, it is possible either to exploit an intrinsic optical property of the polymer or of the composite when it has one (absorbance, IR spectrum, etc.) or to give this polymer or this composite a particular optical property by coupling with a suitable marker, for example a fluorescent or luminescent marker.

Moreover, it is also possible to combine within the same device or "multisensor" several sensors comprising sensitive materials that are different from each other, or equipped with substrates and measuring systems that are different from each other, for instance one or more gravimetric sensors and/or one or more resistive sensors, the essential being that at least one of these sensors comprises a polymer or a composite as defined above.

According to yet another preferred arrangement of the invention, the nitro compound(s) intended to be detected by the sensor is(are) chosen from nitroaromatic compounds, nitroamines, nitrosamines and nitric esters, these compounds possibly being in solid, liquid or gaseous (vapors) form.

Examples of nitroaromatic compounds that may be mentioned include nitrobenzene, dinitrobenzene, trinitrobenzene, nitrotoluene, dinitrotoluene, trinitrotoluene, dinitrofluorobenzene, dinitrotrifluoromethoxybenzene, aminodinitrotoluene, dinitrotrifluoromethylbenzene, chlorodinitrotrifluoromethylbenzene, hexanitrostilbene, trinitrophenylmethylnitramine (or tetryl) or trinitrophenol (or picric acid).

Examples of nitramines include cyclotetramethylenetetranitramine (or octogen), cyclotrimethylenetrinitramine (or hexogen) and tetryl, while an example of a nitrosamine is nitrosodimethylamine.

As regards the nitric esters, they are, for example, pentrite, ethylene glycol dinitrate, diethylene glycol dinitrate, nitroglycerine or nitroguanidine.

Sensors comprising a polymer or a composite as defined above, as sensitive material, have been found to have many advantages, especially:

- an ability to detect nitro compounds, and in particular nitroaromatic compounds, with very high sensitivity since they are capable of detecting their presence at concentrations of the ppm (part per million) order, or even of the tenth of a ppm order,
- rapid response and reproducibility of this response,
- ability to function continuously,
- stability of the performance over time,
- very satisfactory service life,
- manufacturing cost compatible with a production of sensors in series, a very small amount of polymer or of composite (i.e., in practice a few mg) being necessary for the manufacture of a sensor, and
- possibility of being miniaturized and, consequently, of being easily transportable and handleable on all types of sites.

They are therefore particularly useful for detecting explosives, especially in public places.

Other characteristics and advantages of the invention will emerge more clearly on reading the additional description that follows, which relates to examples of using thin films of polytrifluoropropylmethylsiloxane and of polycyanopropylmethylsiloxane in quartz microbalance sensors for the detection of dinitrotrifluoromethoxybenzene (DNTFMB) and dinitrobenzene (DNB) vapors, and which refers to the attached drawings.

The choice of DNTFMB and of DNB as nitro compounds to be detected was driven by the fact that these compounds are very similar to dinitrotoluene (DNT), which is the nitro derivative most commonly present in the chemical signature of mines based on trinitrotoluene (TNT).

Needless to say, the examples that follow are given merely as illustrations of the subject of the invention and do not in any way constitute a limitation of this subject.

EXAMPLES

Example 1

Detection of DNTFMB by a Sensor Comprising a Thin Film of Polytrifluoropropylmethylsiloxane In this example, a quartz microbalance sensor is used, comprising a quartz of cross section AT, with a vibration frequency of 9 MHz, covered with two circular gold measuring electrodes (model QA9RA-50, Ametek Precision Instruments) and bearing on its two faces a thin film of polytrifluoropropylmethylsiloxane.

This film is deposited by spraying a solution of polytrifluoropropylmethylsiloxane (from the company ABCR, reference FMS-9921) in chloroform, with a concentration equal to 5 g/l, 6 times for 0.5 seconds each onto each face of the quartz.

The variation in the vibration frequency of the quartz due to this deposition is 8.1 kHz.

The sensor is subjected to two cycles of exposure to DNTFMB vapors, at room temperature:

the first cycle comprising a phase of exposure to ambient air for 5800 seconds, followed by a phase of exposure to the DNTFMB vapors for 600 seconds, and then a phase of exposure to ambient air for 2600 seconds;

the second cycle comprising a phase of exposure to DNTFMB vapors for 600 seconds, followed by a phase of exposure to ambient air for 4800 seconds; the DNTFMB concentration being 3 ppm in the two cycles.

Figure 1:
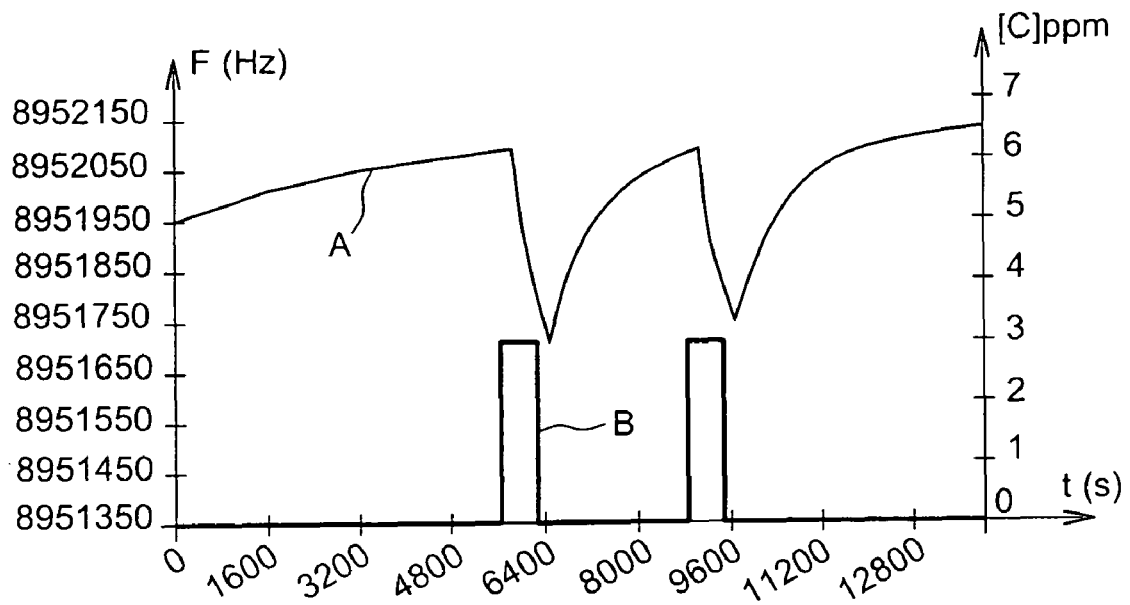
FIG. 1 represents the change in the vibration frequency (curve A) of the quartz of a quartz microbalance sensor comprising a thin film of polytrifluoropropylmethylsiloxane in the course of two cycles of exposure (curve B) of this sensor to DNTFMB vapors at a concentration equal to 3 ppm.

FIG. 1 shows the change in the vibration frequency of the quartz in the course of these two cycles, curve A and curve B corresponding to the respective variations of said frequency (F), expressed in hertz (Hz), and of the concentration of DNTFMB ([C]), expressed in ppm, as a function of the time (t), expressed in seconds.

Example 2

Detection of DNB with a Sensor Comprising a Thin Film of Polytrifluoropropylmethylsiloxane In this example, a quartz microbalance sensor is used comprising a quartz identical to that used in Example 1, but in which the quartz is covered on both faces with a thin film of polytrifluoropropylmethylsiloxane slightly thicker than that used in Example 1.

This film is deposited by spraying a solution of polytrifluoropropylmethylsiloxane in chloroform, with a concentration equal to 2 g/l, 19 times for 0.2 second each onto each face of the quartz.

The variation in the vibration frequency of the quartz due to this deposit is 9.9 kHz.

The sensor is subjected to two cycles of exposure to DNB vapors, at room temperature:

the first cycle comprising a phase of exposure to ambient air for 1700 seconds, followed by a phase of exposure to the DNB vapors for 600 seconds, and then a phase of exposure to ambient air for 2300 seconds;

the second cycle comprising a phase of exposure to DNB vapors for 600 seconds, followed by a phase of exposure to ambient air for 1800 seconds; the DNB concentration being 150 ppb in the two cycles.

Figure 2:
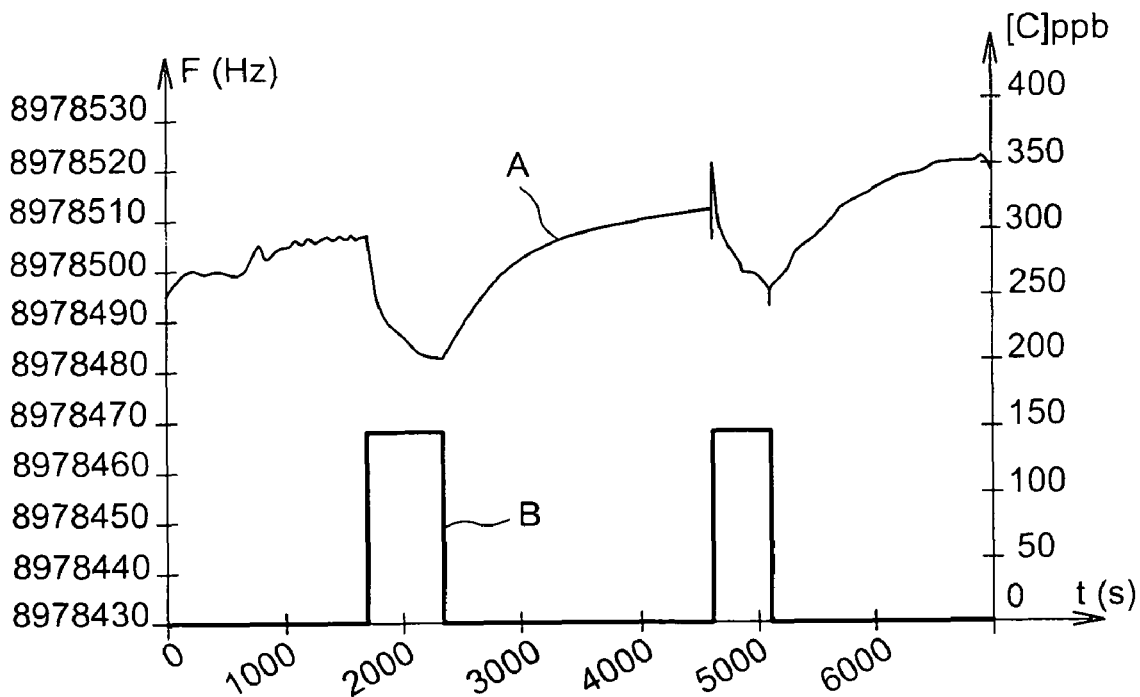
FIG. 2 represents the change in the vibration frequency (curve A) of the quartz of a quartz microbalance sensor comprising a thin film of polytrifluoropropylmethylsiloxane in the course of two cycles of exposure (curve B) of this sensor to DNB vapors at a concentration equal to 150 ppb (parts per billion).

FIG. 2 shows the change in the vibration frequency of the quartz in the course of these two cycles, curve A and curve B corresponding to the respective variations in said frequency (F), expressed in Hz, and in the DNB concentration ([C]), expressed in ppb, as a function of time (t), expressed in seconds.

Example 3

Detection of DNTFMB with a Sensor Comprising a Thin Film of Polycyanopropylmethylsiloxane In this example, a quartz microbalance sensor is used comprising a quartz identical to that used in Example 1, but in which the quartz is covered on both faces with a thin film of polycyanopropylmethylsiloxane.

This film is deposited by spraying a solution of polycyanopropylmethylsiloxane (from the company ABCR, reference YMS-T31) in chloroform, with a concentration equal to 5 g/l, 12 times for 0.2 second each onto each face of the quartz.

The variation in the vibration frequency of the quartz due to this deposit is 8.5 kHz.

The sensor is subjected to a cycle of exposure to DNTFMB vapors with a concentration equal to 3 ppm, at room temperature, this cycle comprising a phase of exposure to ambient air for 3000 seconds, followed by a phase of exposure to DNTFMB vapors for 600 seconds, and then a phase of exposure to ambient air for 11400 seconds.

Figure 3:
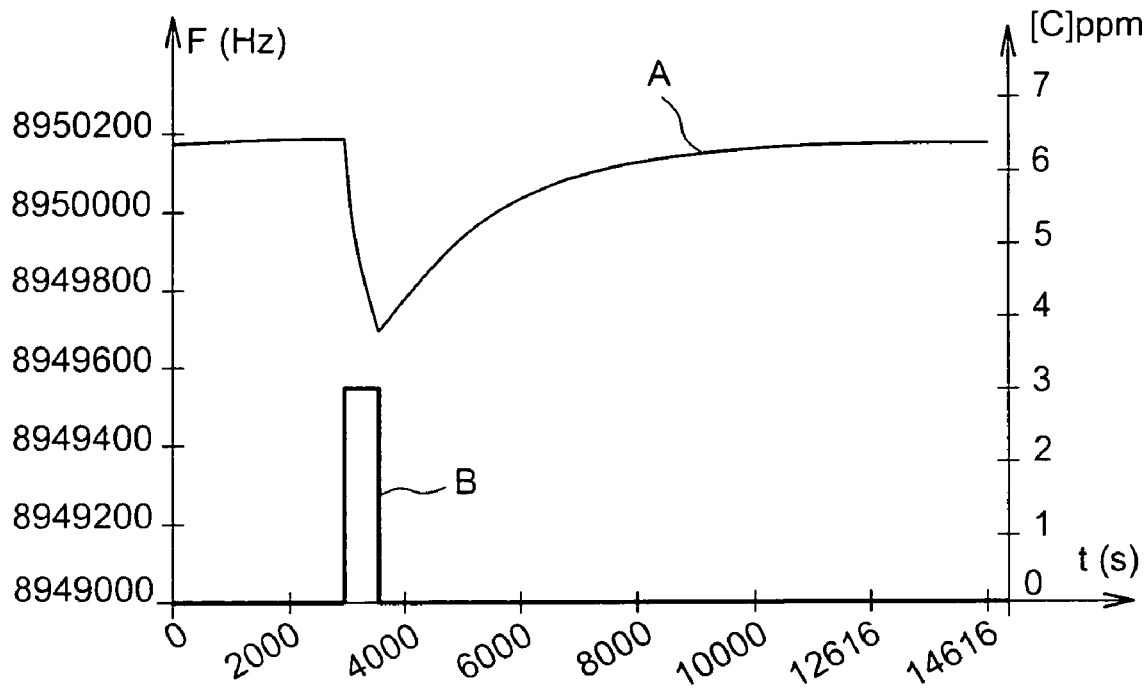
FIG. 3 represents the change in the vibration frequency (curve A) of the quartz of a quartz microbalance sensor comprising a thin film of polycyanopropylmethylsiloxane in the course of a cycle of exposure (curve B) of this sensor to DNTFMB vapors at a concentration equal to 3 ppm.

FIG. 3 shows the change in the vibration frequency of the quartz during this cycle, curve A and curve B corresponding to the respective variations in said frequency (F), expressed in Hz, and in the DNTFMB concentration ([C]), expressed in ppm, as a function of time (t), expressed in seconds.

Example 4

Detection of DNTFMB by a Sensor Comprising a Thin Film of Polycyanopropylmethylsiloxane In this example, a quartz microbalance sensor is used comprising a quartz identical to that used in Example 1, but in which the quartz is covered on both faces with a thin film of polycyanopropylmethylsiloxane.

This film is deposited by spraying a solution of polycyanopropylmethylsiloxane (from the company ABCR, reference YMS-T31) in chloroform, with a concentration equal to 5 g/l, twice for 0.5 second each onto each face of the quartz.

The variation in the vibration frequency of the quartz due to this deposit is 2 kHz.

The sensor is subjected to two cycles of exposure to DNTFMB in the form of vapors, at room temperature:

the first cycle comprising a phase of exposure to ambient air for 1300 seconds, followed by a phase of exposure to DNTFMB at a concentration of 1 ppm for 600 seconds, and then a phase of exposure to ambient air for 6400 seconds;

the second cycle comprising a phase of exposure to DNTFMB at a concentration of 0.1 ppm for 600 seconds, followed by a phase of exposure to ambient air for 1100 seconds.

Figure 4:
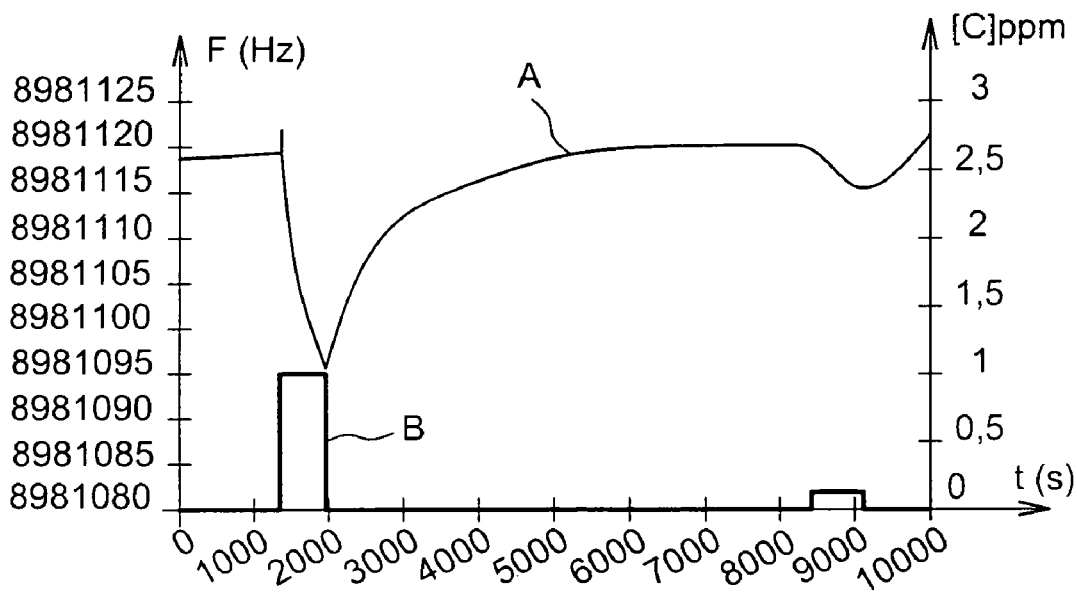
FIG. 4 represents the change in the vibration frequency (curve A) of the quartz of a quartz microbalance sensor comprising a thin film of polycyanopropylmethylsiloxane in the course of two cycles of exposure (curve B) of this sensor to DNTFMB vapors at a concentration equal to 1 ppm for the first cycle and 0.1 ppm for the second.

FIG. 4 shows the change in the vibration frequency of the quartz during these cycles, curve A and curve B corresponding to the respective variations in said frequency (F), expressed in hertz (Hz), and in the DNTFMB concentration ([C]), expressed in ppm, as a function of time (t), expressed in seconds.

Example 5

Study of the Stability Over Time of the Performance of a Sensor Comprising a Thin Film of Polycyanopropylmethylsiloxane In this example, a quartz microbalance sensor equal to that used in Example 4 is used.

This sensor is subjected to a first exposure to DNTFMB vapors at a concentration equal to 3 ppm, at room temperature for 10 minutes, and it is then stored in ambient air.

It is then subjected to eleven other exposures to DNTFMB vapors at a concentration equal to 3 ppm, still at room temperature and for a duration of 10 minutes each, spread over a period of 150 days.

Figure 5:
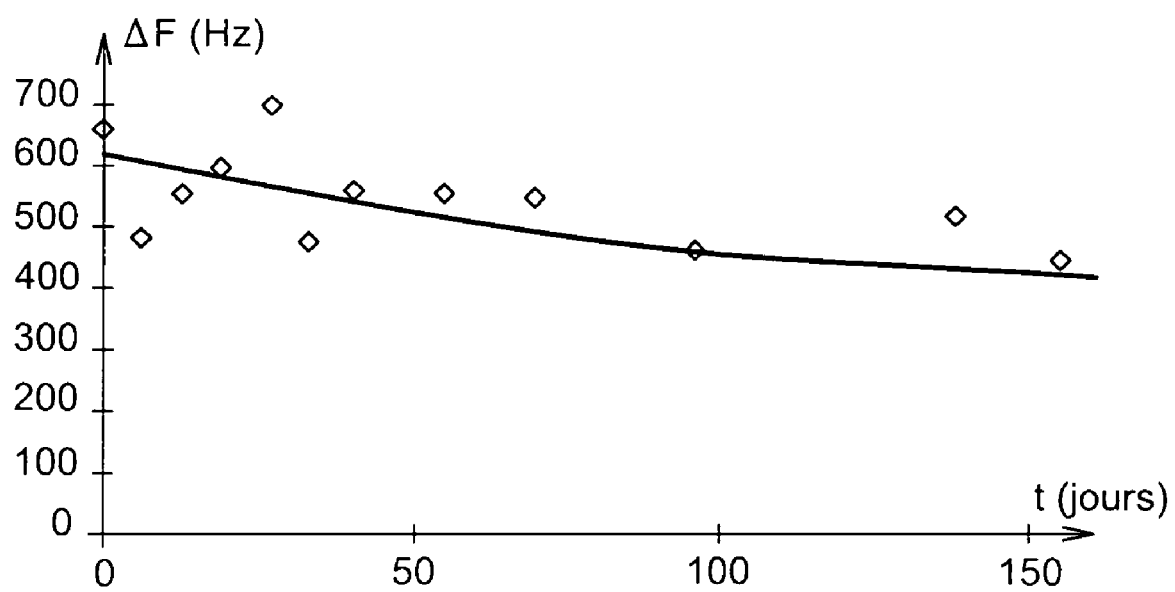
FIG. 5 represents the values of the variations in the vibration frequency ($\Delta F$) of the quartz of a quartz microbalance sensor comprising a thin film of polycyanopropylmethylsiloxane as obtained by subjecting this sensor to twelve exposures to DNTFMB vapors for 10 minutes each, over a period of 150 days.

FIG. 5 represents the values of the variations in the vibration frequency ($\Delta F$) of the quartz observed during these twelve exposures, these values being determined for each exposure as follows:

$\Delta F$=vibration frequency at time $t_0$ of the exposure–vibration frequency at time $t_{10min}$ of the exposure, and symbolized by diamonds on said FIG. 5.

Example 6

Comparison of the Performance of a Sensor Comprising a Thin Film of a Polysiloxane that is Useful According to the Invention and of a Sensor Comprising a Thin Film of a Polysiloxane Recommended by McGill et al.

In this example, two quartz microbalance sensors are used both comprising a quartz identical to that used in Example 1, but differing from each other in that the quartz of the first is coated on both faces with a thin film of polycyanopropylmethylsiloxane, whereas the quartz of the second is coated with a thin film of a polysiloxane whose monomers comprise an aromatic ring and two HFIP side groups.

This polysiloxane corresponds to formula (II) below:

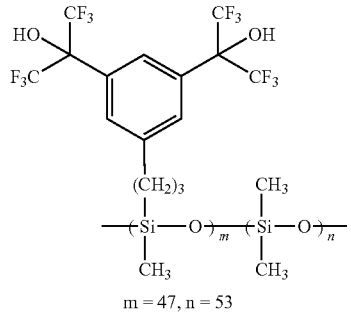

m = 47, n = 53

The films are deposited such that the variation in the vibration frequency of the quartzes due to these deposits is equal to 2 kHz for each of the sensors.

To do this, the polycyanopropylmethylsiloxane film is deposited as described in Example 4, whereas the film of the polysiloxane of formula (II) is deposited by spraying a solution of said polysiloxane in dichloromethane, with a concentration equal to 2 g/l, 6 times for 0.2 second onto both faces of the quartz.

The two sensors are exposed, under exactly the same conditions, to DNTFMB vapors at a concentration equal to 3 ppm, at room temperature for 10 minutes.

The measurement of the vibration frequency of the quartz of the two sensors at time $t_0$ and at time $t_{10\,min}$ of this exposure gives a variation in the vibration frequency of 600 Hz for the quartz of the sensor comprising the thin film of polycyanopropylmethylsiloxane, and of 200 Hz—i.e. 3 times smaller—for the quartz of the sensor comprising the thin film of the polysiloxane of formula (II).

Examples 1 to 4 above show that sensors comprising a sensitive material in accordance with the invention are capable of detecting with very great sensitivity nitro compounds such as DNTFMB and DNB. They also show that the response of these sensors is both reversible and reproducible.

Example 5 furthermore shows that the performance of these sensors is stable over time and that they are still capable, five months after their production, of detecting very small amounts of DNTFMB.

Finally, Example 6 shows that these sensors have, with regard to nitroaromatic compounds, very markedly higher sensitivity than that of a sensor comprising a thin film of a polysiloxane as recommended by McGill et al.

CITED REFERENCES

[1] Content et al., *Chem. Eur. J.*, 6, 2205, 2000
[2] Sanchez-Pedrono et al., *Anal. Chim. Acta*, 182, 285, 1986
[3] Yang et al., *Langmuir*, 14, 1505, 1998
[4] Nelli et al., *Sens. Actuators B*, 13-14, 302, 1993
[5] Yang et al., *J. Am. Chem. Soc.*, 120, 11864, 1998
[6] McGill et al., *Sensors and Actuators* B65, 5-9, 2000

The invention claimed is:

1. A method for detecting the presence of at least one nitro compound in a medium, comprising:

contacting said medium with a sensor comprising a substrate having two faces, wherein at least one of the two faces is covered with a sensitive material having at least one physical property which is modified on contact with nitro compounds, wherein said sensitive material is at least one polymer comprising at least one siloxane repeating unit corresponding to the general formula (I) below:

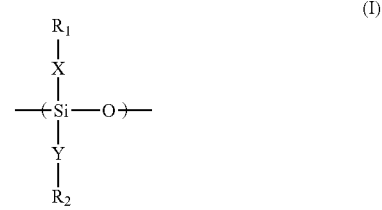

in which:

X and Y, which may be identical or different, represent a single bond or a saturated or unsaturated, linear hydrocarbon group containing from 1 to 50 carbon atoms;

$R_1$ and $R_2$, which may be identical or different, represent a hydrogen atom, a CN group, a group $C(Z)_3$, $CH(Z)_2$ or CH₂Z with Z representing a halogen atom; an NH₂ group, a group NHR₃ or NR₃R₄ with R₃ and R₄ representing, independently of each other, a halogen atom, a methyl group or a linear or branched, saturated or unsaturated hydrocarbon chain containing from 2 to 20 carbon atoms and possibly one or more heteroatoms and/or one or more chemical functions comprising at least one heteroatom; on condition, however, that at least one from among R₁ and R₂ is not a hydrogen atom;

or a composite comprising said polymer and one or more electrically conductive fillers, said sensor providing a first response when no nitro compounds are present in the medium and providing a second different response when at least one nitro compound is present in the medium, said second different response corresponding to a modification of the physical property of the sensitive material on contact with the nitro compound;

measuring a change in the response of the sensor and correlating the change of response to the presence of the nitro compound in the medium.

2. The method of claim 1, in which the siloxane repeating unit corresponds to the formula (Id) below:

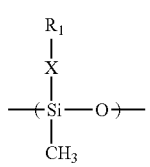

(Id)

in which X is a saturated or unsaturated linear hydrocarbon group containing from 1 to 50 carbon atoms, while R₁ has the same meaning as above.

3. The method of claim 2, in which, in the formula (Id), X represents an alkylene chain containing from 2 to 10 carbon atoms.

4. The method of claim 1, in which the siloxane repeating unit is trifluoropropylmethylsiloxane or cyanopropylmethylsiloxane.

5. The method of claim 1, in which the polymer is chosen in the group consisting of polytrifluoropropylmethylsiloxanes and polycyanopropylmethylsiloxanes.

6. The method of claim 5, in which the polymer has an average molecular weight ranging from 50 to 100 000.

7. The method of claim 1, in which the conductive filler(s) of the composite is(are) chosen in the group consisting of carbon black particles and metal and metal oxide powders.

8. The method of claim 1, in which the polymer or the composite is in the form of a thin film covering one or both faces of the substrate.

9. The method of claim 8, in which the thin film is from 10 angstroms to 100 microns thick.

10. The method of claim 8, in which the thin film is prepared via a technique chosen in the group consisting of spraying, spin coating, drop coating, dip coating, the Langmuir-Blodgett technique, electroplating and in situ polymerization of a precursor monomer of the polymer.

11. The method of claim 1, in which the physical property of the sensitive material which is modified on contact with the nitro compound is the mass of the polymer or the electrical conductivity of the composite.

12. The method of claim 1, in which the sensor is a gravimetric sensor.

13. The method of claim 12, in which the sensor is a quartz microbalance sensor.

14. The method of claim 1, in which the sensor is a resistive sensor.

15. The method of claim 1, in which the nitro compound to be detected is chosen in the group consisting of nitroaromatic compounds, nitroamines, nitrosamines and nitric esters.

16. The method of claim 1, in which the nitro compound to be detected is in solid, liquid or gaseous form.

17. The method of claim 1, in which the nitro compound to be detected is chosen in the group consisting of nitrobenzene, dinitrobenzene, trinitrobenzene, nitrotoluene, dinitrotoluene, trinitrotoluene, dinitrofluorobenzene, dinitrotrifluoromethoxybenzene, aminodinitrotoluene, dinitrotrifluoromethylbenzene, chlorodinitrotrifluoromethylbenzene, hexanitrostilbene, trinitrophenylmethylnitramine and trinitrophenol.

18. The method of claim 1, in which the nitro compound to be detected is a component of explosives.

19. A method for detecting the presence of at least one nitro compound in a medium, comprising:

contacting said medium with a sensor comprising a substrate having two faces, wherein at least one of the two faces is covered with a sensitive material having at least one physical property which is modified on contact with nitro compounds, wherein said sensitive material is at least one polymer comprising at least one siloxane repeating unit corresponding to the formula (Id) below:

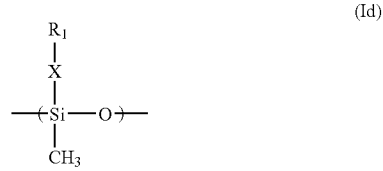

(Id)

in which:

X is a saturated or unsaturated linear hydrocarbon group containing from 1 to 50 carbon atoms, R₁ represents a hydrogen atom, a CN group, a group C(Z)₃, CH(Z)₂ or CH₂Z with Z representing a halogen atom;

or a composite comprising said polymer and one or more electrically conductive fillers, said sensor providing a first response when no nitro compounds are present in the medium and providing a second different response when at least one nitro compound is present in the medium, said second different response corresponding to a modification of the physical property of the sensitive material on contact with the nitro compound;

measuring a change in the response of the sensor and correlating the change of response to the presence of the nitro compound in the medium.

* * * * *